United States Patent [19]
Zhou et al.

[11] Patent Number: 6,037,449
[45] Date of Patent: Mar. 14, 2000

[54] OSTEOMETRIN RELATED PEPTIDES AND NUCLEIC ACIDS AND DIAGNOSIS AND THERAPIES USING THEM

[75] Inventors: Hai-Yan Zhou, Allston; Erdjan Salih, Plymouth; Melvin J. Glimcher, Boston, all of Mass.

[73] Assignee: The Children's Medical Center Corporation, Boston, Mass.

[21] Appl. No.: 08/951,944

[22] Filed: Oct. 17, 1997

Related U.S. Application Data

[60] Provisional application No. 60/028,682, Oct. 18, 1996.

[51] Int. Cl.$^7$ ....................................................... C07K 1/00
[52] U.S. Cl. ............................................................. 530/350
[58] Field of Search .............................................. 530/350

[56] References Cited

U.S. PATENT DOCUMENTS 5,166,058  11/1992  Wang et al. .
5,552,281   9/1996  Stashenko et al. .

OTHER PUBLICATIONS

Sakai et al. EMBO J. 13(16), 3748–56, 1994.

Celeste et al., "Identification of Transforming Growth Factor β Family Members Present in Bone–inductive Protein Purified from Bovine Bone", Proc. Natl. Acad. Sci. 87:9843–9847, 1990.

Ohno et al., "A cDNA Cloning of Human AEBP1 from Primary Cultured Osteoblasts and Its Expression in a Differentiating Osteoblastic Cell Line", Biochemical and Biophysical Res. Comm. 228:411–414, 1996.

Delmas et al., "Identification of the Noncollagenous Proteins of Bovine Bone by Two–Dimensional Gel Electrophoresis", Calcif Tissue Int 36:308–316, 1984.

Laver et al., "Epitopes on Protein Antigens: Misconceptions and Realities", Cell 61:553–556, 1990.

Linde et al., "Mineral Induction by Immobilized Polyanionic Proteins", Calcif Tissue Int 44:286–295, 1989.

Uchiyama et al. "Isolation and Chemical Characterization of the Phosphoproteins of Chicken Bone Matrix: Heterogeneity in Molecular Weight and Composition", Biochemistry 25:7572–7583, 1986.

Zhou et al., "Stimulation by Bone Sialoprotein of Calcification in Osteoblast–Like MC3T3–E1 Cells", Calci Tissue Int 56:403–407, 1995.

*Primary Examiner*—Paula K. Hutzell
*Assistant Examiner*—Lin Sun-Hoffman
*Attorney, Agent, or Firm*—Fish & Richardson P.C.

[57] ABSTRACT

Bovine bone cells express osteometrin, a 35 kDA phosphoprotein specifically expressed in bone and dentin tissue. We have found that protein reactive with anti-osteometrin antisera is detectable in a wide range of species, and that osteometrin expression is detectable during mineralization of bone tissue. Our findings establish that osteometrin is an indicator of bone metabolism and may be involved in highly conserved aspects of bone and dentin metabolism. Osteometrin is used as a marker for osteoporosis and bone cancer.

3 Claims, 4 Drawing Sheets

Protocol for extraction of bone

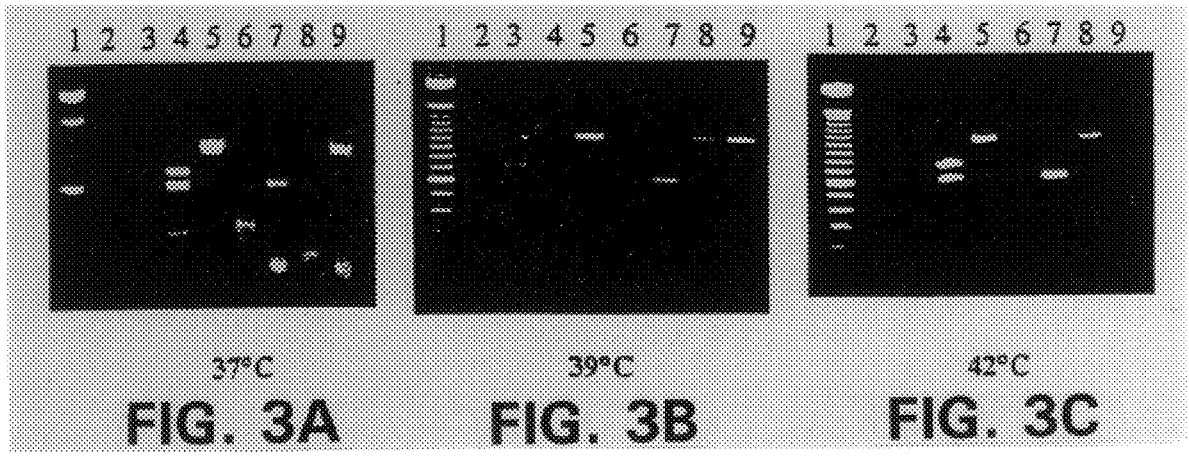
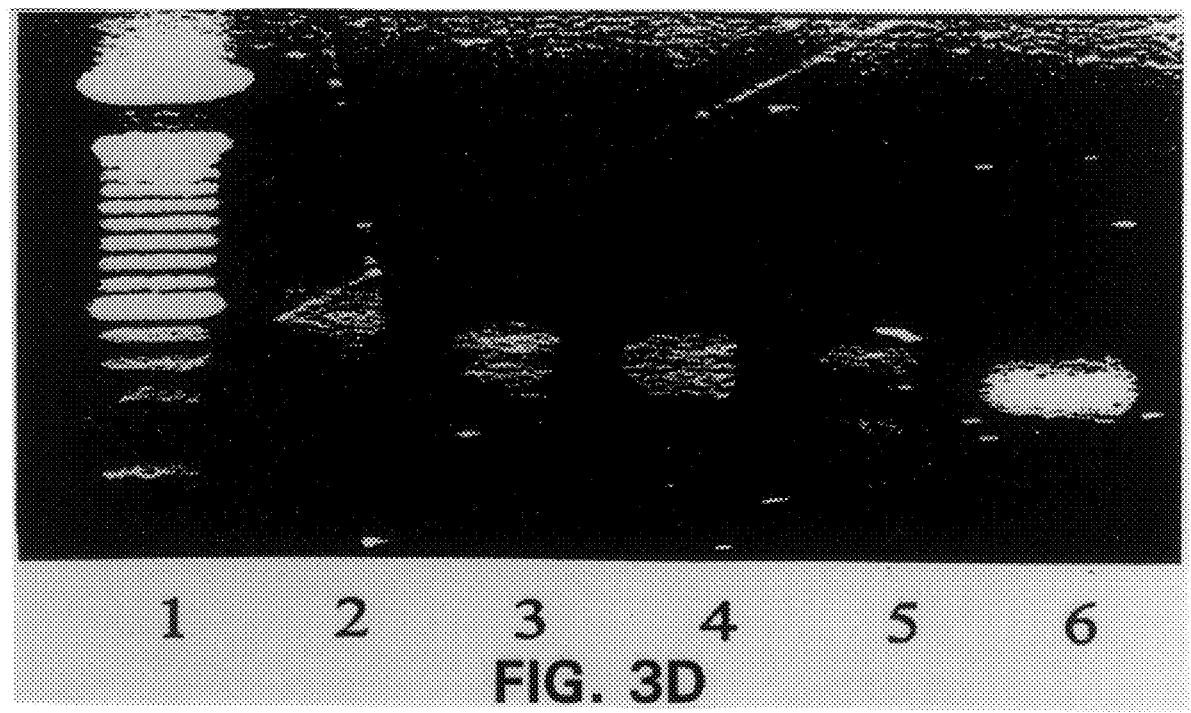

```
                          SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:1:

Ser Tyr Pro Tyr Asn Pro Gln Xaa Xaa Met Asn Ile Tyr Xaa Xaa Tyr
  1               5                  10                  15

Xaa Trp Phe Tyr Xaa
             20

(2) INFORMATION FOR SEQ ID NO:2:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:2:

Asn Xaa Asp Xaa Met Xaa Gly
  1               5

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:3:

Asn Xaa Xaa Leu Xaa Xaa Xaa Xaa Val Asp Phe Pro Xaa Tyr
  1               5                  10

(2) INFORMATION FOR SEQ ID NO:4:

(i) SEQUENCE CHARACTERISTICS:
        (A) LENGTH: 4 amino acids
        (B) TYPE: amino acid
        (D) TOPOLOGY: linear (ii) MOLECULE TYPE: peptide
```

(xi) SEQUENCE DESCRIPTION: SEQ ID NO:4:

Val Xaa Met Xaa
1

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:5:

Ala Xaa Phe Gly Xaa Xaa Xaa Xaa Pro Val Gln Pro Pro Gly
1               5                   10

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:6:

Tyr Ala Gly Tyr Asn Ala Tyr Ala Glu Gly
1               5                   10

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:7:

Asn Xaa Xaa Pro Asn Asn Met Pro Xaa Gly Pro
1               5                   10

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:8:

Ser Tyr Pro Tyr Asn Pro Gln Tyr Met Asn Ile
1               5                   10

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:9:

TAYCCNTAYA AYCCNYADCA RTAYATGAA                                              29

(2) INFORMATION FOR SEQ ID NO:10:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:10:

```
Ser Tyr Pro Tyr Asn Pro Tyr Val Tyr Met Asn Ile
  1               5                  10
```

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:11:

```
TAYCCNTAYA AYCCNTAYGT NTAYATGAA                              29
```

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:12:

```
Asn Tyr Asp Met Gly
  1               5
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:13:

```
AAYTAYGAYG AYATGGGNGG                                        20
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:14:

```
CCNCCCATRT CRTCRTARTT                                        20
```

(2) INFORMATION FOR SEQ ID NO:15:

```
    (i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:15:

Asn Met Tyr Leu Phe Gly Met Leu Val
 1               5

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:16:

AAYATGTAYY TDTTYGGNAT GYTDGTN                                     27

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:17:

NACHARCATN CCRAAHARRT ACATRTT                                     27

(2) INFORMATION FOR SEQ ID NO:18:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:18:

Ala Ser Phe Gly Leu Glu Asp Pro Val Gln
 1               5

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:19:

TTYGGNYTDG ARGAYCCNCC NGT                                         23

(2) INFORMATION FOR SEQ ID NO:20:

(i) SEQUENCE CHARACTERISTICS:
        (A) LENGTH: 10 amino acids
        (B) TYPE: amino acid
        (D) TOPOLOGY: linear
```

-continued

```
        (ii) MOLECULE TYPE: peptide (xi) SEQUENCE DESCRIPTION: SEQ ID NO:20:

Tyr Ala Gly Tyr Met Ala Tyr Ala Glu Gly
  1               5                  10

(2) INFORMATION FOR SEQ ID NO:21:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:21:

GGNTAYATGG CNTAYGCNGA RGG                                             23

(2) INFORMATION FOR SEQ ID NO:22:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: primer (xi) SEQUENCE DESCRIPTION: SEQ ID NO:22:

CCYTCNGCRT ANGCCATRTA NCC                                             23
```

OSTEOMETRIN RELATED PEPTIDES AND NUCLEIC ACIDS AND DIAGNOSIS AND THERAPIES USING THEM

CROSS REFERENCE TO RELATED APPLICATION

This application claims benefit from provisional application Ser. No. 60/028,682 filed Oct. 18, 1996.

STATEMENT AS TO FEDERALLY SPONSORED RESEARCH

This work was supported in part by grant AR34074 from the National Institutes of health.

BACKGROUND OF THE INVENTION

Various proteinaceous components of bone and dentin have been identified. Some of those components, such as collagen, are major structural components and are also present in soft tissues of the body. Noncollagenous proteins (10%) may play functional roles specific to bone and dentin, such as initiation of mineralization and control of calcium phosphate crystal growth and degradation (Glimcher, in *Disorders of Bone and Mineral Metabolism*, Coe et al., eds., Raven Press, New York, 1992, p. 265–288; Young et al., in *Cellular and Molecular Biology of Bone*, Noda, ed., Academic Press, San Diego, 1993, p. 191–234; Heinegard et al., FASEB J. 2:2041–51, 1989; Delmas et al., Calcif. Tissue Int. 36:308–16, 1983). Major noncollagenous extracellular matrix proteins include osteocalcin, osteonectin, osteopontin, bone sialoprotein, decorin, and biglycan (Glimcher, 1992, supra; Young et al., 1993, supra,; Heinegard et al., 1989, FASEB J. 2, 2041–51). Common clinically used bone markers include osteocalcin, type I collagen, pyridinoline, dexoxypyridinoline, and alkaline phosphatase (Delmas, 1993, in *Primer on the Metabolic Bone Diseases and Disorders of Mineral Metabolism*, Favus, ed., 2nd Ed., Lippincott-Raven Publishers, Philadelphia).

In some contexts, it is desirable to distinguish bone from soft tissue. Specificity of bone markers may be reduced if the marker is also expressed in soft tissue or if antibodies to it react with moieties found in soft tissue, including fragments or degradation products of a marker specifically expressed in bone. For example, while osteocalcin is bone-specific, some osteocalcin antibodies have been shown to also react to some extent with matrix Gla-containing protein, which is distributed in many soft tissues in addition to bone (Hauschka et al., 1989, Physiol. Rev. 69, 990–1047).[1] Osteocalcin protein fragments are also present in blood because of bone resorption. Thus, serum osteocalcin levels may not reflect bone formation. In addition, because most osteocalcin is excreted from kidney, osteocalcin levels in individuals with kidney diseases may not accurately reveal the state of bone metabolism.

[1] The abbreviations used are: BSA, bovine serum albumin; FcαR, Fc receptor for Ig; Gdn, guanidine; Gla, carboxyglutamic acid; HPLC, high performance liquid chromatography; Ig, immunoglobulin; Mab, monoclonal antibody; PAGE, SDS-polyacrylamide gel electrophoresis; PCR, polymerase chain reaction; RT, reverse transcriptase; RP, reversed phase.

SUMMARY OF THE INVENTION

We have discovered a protein, osteometrin, that is expressed almost exclusively in bone and dentin tissue in a wide range of species, is expressed during calcification of bone tissue, and is over-expressed in osteoporotic patients.

In addition to the specific osteometrin sequences provided (or cross-referenced) herein, relevant molecules include fragments of those sequences and related polypeptides described elsewhere. These polypeptides (and non-peptide mimetics), as well as nucleic acids encoding them, can be used for a variety of diagnostic and therapeutic applications for bone-associated diseases.

One embodiment of the invention generally features a substantially pure mammalian osteometrin polypeptide. Preferably, the osteometrin polypeptide includes the following amino acid sequences:

N-terminal sequence: Ser Tyr Pro Tyr Asn Pro Gln $Xaa_1$ $Xaa_2$ Met Asn Ile Tyr $Xaa_3$ $Xaa_4$ Tyr $Xaa_5$ Trp Phe Tyr $Xaa_6$ (SEQ ID NO:1), where $Xaa_1$ is Tyr or Gln, $Xaa_2$ is Val or Tyr, $Xaa_3$ is Asp or Pro, $Xaa_4$ is Phe or Val, $Xaa_5$ is Asn or Gly, and $Xaa_6$ is Leu, Asn, or Lys;

Internal peptide 1: Asn $Xaa_1$ Asp $Xaa_2$ Met $Xaa_3$ Gly (SEQ ID NO:2), where $Xaa_1$ is Asp or Tyr, $Xaa_2$ is Tyr, Met, or Asp, and $Xaa_3$ is Asp or Gly;

Internal peptide 2: Asn $Xaa_1$ $Xaa_2$ Leu $Xaa_3$ $Xaa_4$ $Xaa_5$ $Xaa_6$ Val Asp Phe Pro $Xaa_7$ Tyr (SEQ ID NO:3), where $Xaa_1$ is Val, Pro, or Met, $Xaa_2$ is Gln or Tyr, $Xaa_3$ is Glu or Pro, $Xaa_4$ is Gln or Gly, $Xaa_5$ is Met or Val, $Xaa_6$ is Gln, Asp, or Pro, and Xaa7 is Tyr or Pro;

Internal peptide 3: Val $Xaa_1$ Met $Xaa_2$ (SEQ ID NO:4), where $Xaa_1$ is Met, Gly, or Ala and $Xaa_2$ is Gly, Leu, or Tyr;

Internal peptide 4: Ala $Xaa_1$ Phe Gly $Xaa_2$ $Xaa_3$ $Xaa_4$ $Xaa_5$ Pro Val Gln Pro Pro Gly (SEQ ID NO:5), where $Xaa_1$ is Val, Glu, or Ser, $Xaa_2$ is Pro or Leu, $Xaa_3$ is Pro or Glu, $Xaa_4$ is Gly or Asp, and $Xaa_5$ is Val or Pro;

Internal peptide 5: Tyr Ala Gly Tyr Asn Ala Tyr Ala Glu Gly (SEQ ID NO:6); and

Internal peptide 6: Asn $Xaa_1$ $Xaa_2$ Pro Asn Asn Met Pro $Xaa_3$ Gly Pro (SEQ ID NO:7), where $Xaa_1$ is His or Leu, $Xaa_2$ is Pro or Gly, and $Xaa_3$ is any natural amino acid.

The term "nucleic acid" encompasses both RNA and DNA, including CDNA, genomic DNA, and synthetic (e.g., chemically synthesized or modified) DNA. The nucleic acid may be double-stranded or single-stranded. Where single stranded, the nucleic acid may be a sense strand or an antisense strand. The term "isolated nucleic acid" refers to a nucleic acid which may be flanked by non-natural sequences, such as those of a plasmid or virus. Thus, the nucleic acid can include none, some, or all of the 5' non-coding (e.g., promoter) sequences which are immediately contiguous to the coding sequence. The term, therefore, includes, for example, a recombinant DNA which is incorporated into a vector including an autonomously replicating plasmid or virus, or into the genomic DNA of a prokaryote or eukaryote, or which exists as a separate molecule (e.g., a CDNA or a genomic DNA fragment produced by PCR or restriction endonuclease treatment) independent of other sequences. The term also includes a recombinant DNA or RNA which is part of a hybrid gene encoding an additional polypeptide sequence. Moreover, the term is meant to include nucleic acid fragments which are not naturally occurring as fragments and would not be found in the natural state.

Polypeptides may be processed to yield a mature sequence e.g., lacking a leader sequence. Polypeptides substantially identical to mature osteometrin have an amino acid sequence which is at least 85%, preferably 90%, and most preferably 95% or even 99% identical to the amino acid sequence of the osteometrin polypeptide.

By "substantially identical" is meant a polypeptide or nucleic acid having a sequence that is at least 85%, preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705).

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

By "protein" and "polypeptide" is meant any chain of amino acids, regardless of length or post-translational modification (e.g., glycosylation or phosphorylation).

By "substantially pure" is meant a preparation which is at least 60% by weight (dry weight) the compound of interest, i.e., an osteometrin polypeptide. Preferably the preparation is at least 75%, more preferably at least 90%, and most preferably at least 99%, by weight the compound of interest. Purity can be measured by any appropriate standard method, e.g., column chromatography, polyacrylamide gel electrophoresis, or HPLC analysis followed by detection.

The polypeptides of the invention include, but are not limited to: recombinant polypeptides, natural polypeptides, and synthetic polypeptides as well as polypeptides which are preproteins or proproteins.

The polypeptides of the invention can be expressed fused to another polypeptide, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

Polypeptides corresponding to one or more domains of osteometrin are also within the scope of the invention. Also within the invention are soluble fusion proteins in which a full-length form of osteometrin or a portion (e.g., one or more domains) thereof is fused to an unrelated protein or polypeptide (i.e., a fusion partner) to create a fusion protein.

The invention also features isolated nucleic acid sequences that encode a portion of osteometrin corresponding to one or more domains of osteometrin. Also within the invention are nucleic acids encoding fusion proteins in which a portion of osteometrin or a portion (e.g., one or more domains) thereof is fused to an unrelated protein or polypeptide (i.e., a fusion partner) to create a fusion protein.

Encompassed within the invention are nucleic acid sequences that encode forms of osteometrin in which sequences are altered or deleted.

The nucleic acids of the invention include nucleic acids encoding mature osteometrin as well as osteometrin polypeptides fused to a polypeptide which facilitates secretion, e.g., a secretory sequence. Such a fused protein is typically referred to as a preprotein. The secretory sequence can be removed by the host cell to form the mature protein. Also within the invention are nucleic acids that encode mature osteometrin fused to a polypeptide sequence to produce an inactive preprotein. Preproteins can be converted into the active form of the protein by removal of the inactivating sequence.

The invention also encompasses nucleic acids that hybridize under stringent conditions to a nucleic acid encoding a osteometrin polypeptide. "Stringent conditions" means hybridization at 50° C. in Church buffer (7% SDS, 0.5% $NaHPO_4$, 1 mM EDTA, 1% BSA) and washing at 50° C. in 2× SSC. The hybridizing portion of the hybridizing nucleic acids are preferably 20, 30, 50, or 70 bases long. Preferably, the hybridizing portion of the hybridizing nucleic acid is 95% or even 98% identical to the sequence of a portion of a nucleic acid encoding a osteometrin polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by naturally-occurring osteometrin. Hybridizing nucleic acids can be splice variants encoded by a osteometrin gene. Thus, they may encode a protein which is shorter or longer than the form of osteometrin described herein. Hybridizing nucleic acids may also encode proteins which are related to osteometrin (e.g, proteins encoded by genes which include a portion having a relatively high degree of identity to a osteometrin gene described herein).

The invention also features substantially pure osteometrin polypeptides.

The invention also encompasses polypeptides and nucleic acids whose sequences are substantially identical to that of a form of osteometrin described herein.

The invention features transformed cells harboring a nucleic acid encompassed by the invention. The invention also features vectors and plasmid which include a nucleic acid of the invention which is properly positioned for expression.

By "transformed cell" is meant a cell into which (or into an ancestor of which) has been introduced, by means of recombinant DNA techniques, a DNA molecule encoding (as used herein) osteometrin polypeptide.

By "positioned for expression" is meant that the selected DNA molecule is positioned adjacent to one or more sequence elements which direct transcription and/or translation of the sequence such that the sequence elements can control transcription and/or translation of the selected DNA (i.e., the selected DNA is operably associated with the sequence elements). Such operably associated elements can be used to facilitate the production of an osteometrin polypeptide.

The invention also features purified antibodies which specifically bind an osteometrin protein or polypeptide.

By "purified antibody" is meant an antibody which is at least 60%, by dry weight, free from the proteins and naturally-occurring organic molecules with which it is naturally associated. Preferably, the preparation is at least 75%, more preferably at least 90%, and most preferably at least 99%, by dry weight, antibody.

By "specifically binds" is meant an antibody that recognizes and binds to a particular antigen, e.g., osteometrin polypeptide, but which does not substantially recognize and bind to other molecules in a sample, e.g., a biological sample, which naturally includes osteometrin.

The invention also features antagonists and agonists of osteometrin. Antagonists can inhibit one or more of the functions of osteometrin. Suitable antagonists can include large or small molecules, antibodies to osteometrin, and osteometrin polypeptides which compete with a native form of osteometrin. Agonists of osteometrin will enhance or facilitate one or more of the functions of osteometrin. Suitable agonists can include, for example, large or small molecules and antibodies to osteometrin.

The invention also features a substantially pure polypeptide which includes a first portion and a second portion; the first portion includes a osteometrin polypeptide and the second portion includes a non-osteometrin polypeptide, e.g., a detectable marker.

In another aspect the invention features a recombinant nucleic acid encoding an osteometrin polypeptide.

The invention also features a nucleic acid encoding a hybrid polypeptide. This hybrid polypeptide includes a first portion and a second portion; the first portion includes an osteometrin polypeptide; the second portion includes a non-osteometrin polypeptide.

The invention also feature a cell which harbors a recombinant nucleic acid encoding an osteometrin polypeptide; a vector which includes a nucleic acid encoding an osteometrin polypeptide.

In another aspect the invention features an antibody which selectively binds to an osteometrin polypeptide. In a preferred embodiment the antibody is a monoclonal antibody.

The invention also features a pharmaceutical composition which includes an osteometrin polypeptide.

The invention features a method for detecting bone mineralization, including calcification. This method includes: (a) obtaining a biological sample; (b) contacting the sample with an antibody which selectively binds an osteometrin polypeptide; and (c) determining the amount of the antibody selectively bound to said biological sample as a measure of calcification. In one embodiment, this method is used to measure increased serum levels of osteometrin, which is indicative of osteoporosis in a vertebrate.

In another aspect, the invention features a method for treating inflammation in a patient which includes administering to the patient an agonist of osteometrin.

Also featured are recombinant nucleic acids encoding bovine osteometrin polypeptides and fusion polypeptides, as well as cells or vectors comprising the recombinant nucleic acids.

The invention also features pharmaceutical compositions comprising the osteometrin polypeptides or the nucleic acids.

Other features and advantages of the invention will be apparent from the following detailed descriptions, and from the claims.

BRIEF DESCRIPTION OF THE DRAWINGS

FIGS. 3A–3D are pictures of PCR products after separation on agarose gels.

DETAILED DESCRIPTION

Figure 1:
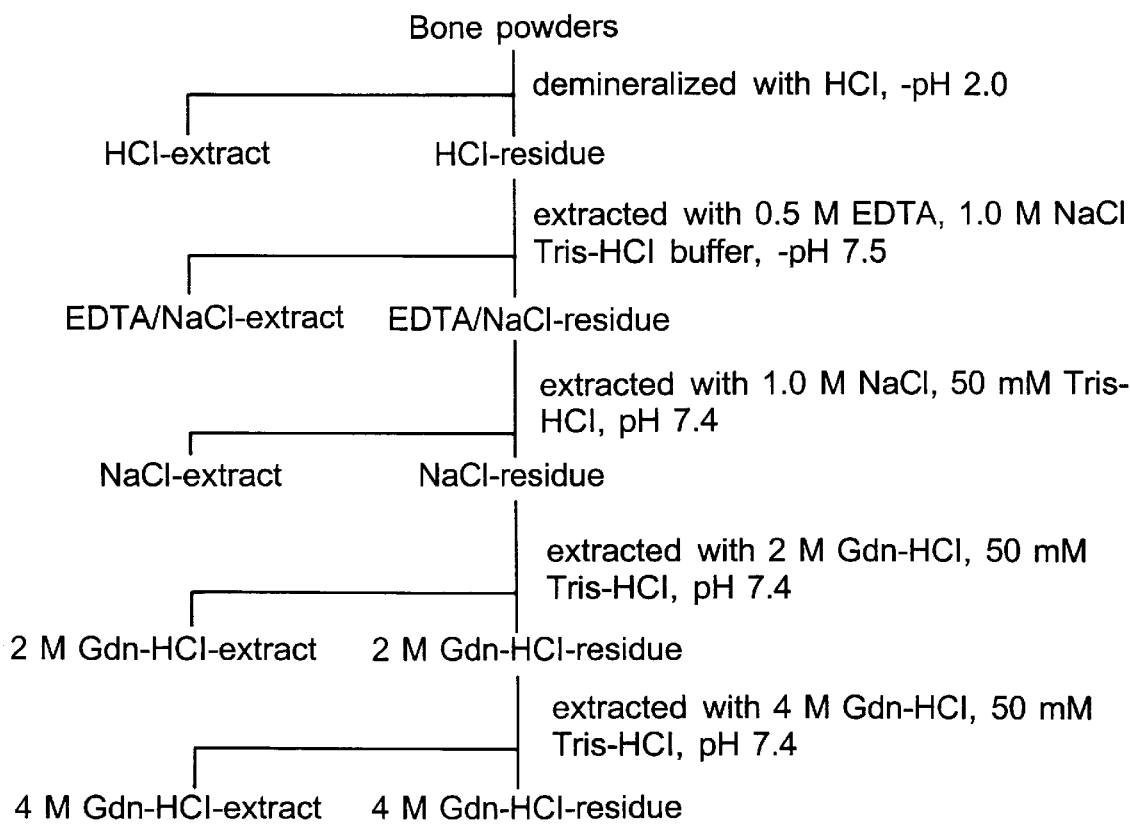
FIG. 1 describes the protocol for extracting osteometrin from bone.

The invention encompasses, but is not limited to, osteometrin proteins and polypeptides that are functionally related to osteometrin.

The invention also encompasses nucleic acid sequences encoding osteometrin polypeptides. Such DNA sequences can be isolated by techniques widely known in the art. For example, oligonucleotide probes can be designed corresponding to the known partial bovine osteometrin amino acid sequence and used to screen CDNA libraries prepared from mRNA isolated from bovine osteometrin expressing tissue (e.g., by the methods described in Sambrook et al., *Molecular Cloning: A Laboratory Manual*, 2 ed., Cold Spring Harbor., 1989). Alternatively, anti-osteometrin antibodies can be used to screen expression libraries prepared from MRNA of cells expressing osteometrin polypeptide in order to obtain osteometrin cDNAs (Sambrook et al., supra). Preferably, any osteometrin CDNA or genomic DNA is cloned by PCR using degenerate primers corresponding to the partial amino acid sequences of osteometrin. Overlapping partial CDNA or genomic DNA clones are used to derive the full length clones by any method known in the art, e.g., PCR.

Without further elaboration, it is believed that one skilled in the art can, based on the above disclosure and the examples described below, utilize the present invention to its fullest extent. The following examples are to be construed as merely illustrative of how one skilled in the art can isolate osteometrin genes and proteins from any vertebrate species, and are not limitative of the remainder of the disclosure in any way whatsoever. Any publications cited in this disclosure are hereby incorporated by reference.

Generating, Expressing and Isolating Osteometrin-derived Proteins

Osteometrin-derived proteins and polypeptides include any protein or polypeptide sharing a functional characteristic with osteometrin. Such functionally related osteometrin polypeptides include, but are not limited to, additions or substitutions of amino acid residues within the amino acid sequence encoded by the osteometrin sequences described herein which result in a silent change, thus producing a functionally equivalent gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Osteometrin variants with altered amino acid sequences can be created by making random mutations to osteometrin DNA using random mutagenesis techniques well known to those skilled in the art. Alternatively, site-directed mutations of the osteometrin coding sequence can be engineered using techniques also well-known to those skilled in the art.

To design variant osteometrin polypeptides, it is useful to distinguish between conserved positions and variable positions. Conserved on variable amino acid residues are determined from an amino acid alignment of at least two osteometrin polypeptides. Conserved amino acids are those that do not change or change infrequently from polypeptide to polypeptide. Variable amino acids are those that frequently change from polypeptide to polypeptide. To produce variants with unaltered osteometrin functions, it is preferable that conserved residues are not altered. Moreover, alteration of non-conserved residues are preferably conservative alterations, e.g., a basic amino acid is replaced by a different basic amino acid. To produce altered function variants, it is preferable to make non-conservative changes at variable and/or conserved positions. Deletions at conserved and variable positions can also be used to create variants.

Other mutations to the osteometrin coding sequence can be made to generate osteometrins that are better suited for expression, e.g., for scaled up production, etc., in a selected host cell. For example, potential N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X-T), and/or an amino acid deletion at the second position of any one or more of such recognition sequences, will prevent glycosylation at the modified tripeptide sequence. (See , e.g., Miyajima et al., EMBO J. 5:1193, 1986).

Preferred osteometrin polypeptides are those polypeptides, or variants thereof, that are involved in, or are indicative of, bone metabolism, such as mineralization. In determining whether a particular osteometrin polypeptide or variant thereof detects or is involved in bone formation, one can use any assay techniques disclosed herein or in referenced publications. Preferred osteometrin polypeptides and variants have 20%, 40%, 50%, 75%, 80%, or even 90% of the activity of the full-length, mature calf form of osteometrin described herein. Such comparisons are generally based on equal concentrations of the molecules being compared. The comparison can also be based on the amount of protein or polypeptide required to reach 50% of the maximal stimulation obtainable.

Preferred polypeptides are those which are soluble under normal physiological conditions. Also within the invention are fusion proteins in which a portion (e.g., one or more domains) of osteometrin is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of osteometrin is joined in-frame to a nucleotide sequence encoding the fusion partner.

In general, osteometrin proteins according to the invention can be produced by transformation (transfection, transduction, or infection) of a host cell with all or part of a osteometrin-encoding DNA fragment in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention. The osteometrin protein can be produced in a prokaryotic host (e.g., *E. coli* or *B. subtilis*) or in a eukaryotic host (e.g., Saccharomyces or Pichia; mammalian cells, e.g., COS, NIH 3T3 CHO, BHK, 293, or HeLa cells; or insect cells).

Proteins and polypeptides can also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al. (*Current Protocols in Molecular Biology*, John Wiley & Sons, New York, 1994); expression vehicles may be chosen from those provided, e.g., in *Cloning Vectors*: A Laboratory Manual (P. H. Pouwels et al., 1985, Supp. 1987).

The host cells harboring the expression vehicle can be cultured in conventional nutrient media adapted as need for activation of a chosen gene, repression of a chosen gene, selection of transformants, or amplification of a chosen gene.

One preferred expression system is the mouse 3T3 fibroblast host cell transfected with a pMAMneo expression vector (Clontech, Palo Alto, Calif.). PMAMNEO provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a osteometrin protein would be inserted into the PMAMNEO vector in an orientation designed to allow expression. The recombinant osteometrin protein would be isolated as described below. Other preferable host cells that can be used in conjunction with the PMAMNEO expression vehicle include COS cells and CHO cells (ATCC Accession Nos. CRL 1650 and CCL 61, respectively).

Alternatively, an insect cell expression system can be used. In an insect cell expression system, Autographa californica nuclear polyhidrosis virus (AcNPV), which grows in *Spodoptera frugiperda* cells, is used as a vector to express foreign genes. A osteometrin coding sequence can be cloned individually into non-essential regions (for example the polyhedrin gene) of the virus and placed under control of an AcNPV promoter, e.g., the polyhedrin promoter. Successful insertion of a gene encoding a osteometrin polypeptide or protein will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed (see, e.g., Smith et al., *J. Virol.* 46:584, 1983; Smith, U.S. Pat. No. 4,215,051).

In mammalian host cells, a number of viral-based expression systems can be utilized. In cases where an adenovirus is used as an expression vector, the osteometrin nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a osteometrin gene product in infected hosts (see, e.g., Logan, Proc. Natl. Acad. Sci. USA 81:3655, 1984).

Specific initiation signals may also be required for efficient translation of inserted nucleic acid sequences. These signals include the ATG initiation codon and adjacent sequences. In cases where an entire native osteometrin gene or CDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., Methods in Enzymol. 153:516, 1987).

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and in particular, choroid plexus cell lines.

Alternatively, osteometrin protein can be produced by a stably-transfected mammalian cell line. A number of vectors suitable for stable transfection of mammalian cells are available to the public, see, e.g., Pouwels et al. (supra); methods for constructing such cell lines are also publicly available, e.g., in Ausubel et al. (supra). In one example, CDNA encoding the osteometrin protein is cloned into an expression vector that includes the dihydrofolate reductase (DHFR) gene. Integration of the plasmid and, therefore, the osteometrin protein-encoding gene into the host cell chromosome is selected for by including 0.01–300 μM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and Padd26sv(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyltransferase, and adenine phosphoribosyltransferase genes can be employed in tk, hgprt, or aprt cells, respectively. In addition, gpt, which confers resistance to mycophenolic acid (Mulligan et al., Proc. Natl. Acad. Sci. USA 78:2072, 1981); neo, which confers resistance to the aminoglycoside G-418 (Colberre-Garapin et al., J. Mol. Biol. 150:1, 1981); and hygro, which confers resistance to hygromycin (Santerre et al., Gene 30:147, 1981), can be used.

Osteometrin polypeptides can also be produced as fusion proteins. For example, the expression vector PUR278 (Ruther et al., *EMBO J*. 2:1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

A fusion protein can be readily purified by utilizing an antibody specific for the fusion protein being expressed. For example, a system described in Janknecht et al., Proc. Natl. Acad. Sci. USA, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, osteometrin or a portion thereof, can be fused to an immunoglobulin Fc domain. Such a fusion protein can be readily purified using an affinity column.

Osteometrin proteins and polypeptides can also be expressed in transgenic animals. Animals of any species, including, but not limited to, mice, rats, rabbits, guinea pigs, pigs, micro-pigs, goats, and non-human primates, e.g., baboons, monkeys, and chimpanzees, can be used to generate osteometrin-expressing transgenic animals.

Any technique known in the art can be used to introduce a osteometrin transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., Proc. Natl. Acad. Sci., USA 82:6148, 1985); gene targeting into embryonic stem cells (Thompson et al., Cell 56:313, 1989); and electroporation of embryos (Lo, Mol. Cell. Biol. 3:1803, 1983).

The present invention provides for transgenic animals that carry the osteometrin transgene in all their cells, as well as animals that carry the transgene in some, but not all of their cells, i.e., mosaic animals. The transgene can be integrated as a single transgene or in concatamers, e.g., head-to-head tandems or head-to-tail tandems The transgene can also be selectively introduced into and activated in a particular cell type (Lasko et al., Proc. Natl. Acad. Sci. USA 89:6232, 1992). The regulatory sequences required for such a cell-type specific activation will depend upon the particular cell type of interest, and will be apparent to those of skill in the art.

When it is desired that the osteometrin transgene be integrated into the chromosomal site of the endogenous osteometrin gene, gene targeting is preferred. Briefly, when such a technique is to be used, vectors containing some nucleotide sequences homologous to an endogenous osteometrin gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous osteometrin gene in only that cell type (Gu et al., Science 265:103, 1984). The regulatory sequences required for such a cell-type specific inactivation will depend upon the particular cell type of interest, and will be apparent to those of skill in the art.

Once transgenic animals have been generated, the expression of the recombinant osteometrin gene can be assayed utilizing standard techniques. Initial screening may be accomplished by Southern blot analysis or PCR techniques to analyze animal tissues to assay whether integration of the transgene has taken place. The level of MRNA expression of the transgene in the tissues of the transgenic animals may also be assessed using techniques which include, but are not limited to, Northern blot analysis of tissue samples obtained from the animal, in situ hybridization analysis, and RT-PCR. Samples of osteometrin gene-expressing tissue, also can be evaluated immunocytochemically using antibodies specific for the osteometrin transgene product.

Once the recombinant osteometrin protein is expressed, it is isolated. Secreted forms can be isolated from the culture media, while non-secreted forms must be isolated from the host cells. Proteins can be isolated by affinity chromatography. In one example, an anti-osteometrin protein antibody (e.g., produced as described herein) is attached to a column and used to isolate the osteometrin protein. Lysis and fractionation of osteometrin protein-harboring cells prior to affinity chromatography can be performed by standard methods (see, e.g., Ausubel et al., supra). Alternatively, a osteometrin fusion protein, for example, a osteometrin-maltose binding protein, a osteometrin-β-galactosidase, or a osteometrin-trpE fusion protein, can be constructed and used for osteometrin protein isolation (see, e.g., Ausubel et al., supra; New England Biolabs, Beverly, Mass.).

Once isolated, the recombinant protein can, if desired, be further purified, e.g., by HPLC using standard techniques (see, e.g., Fisher, *Laboratory Techniques In Biochemistry And Molecular Biology*, eds., Work and Burdon, Elsevier, 1980).

Polypeptides of the invention, particularly short osteometrin fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful osteometrin fragments or analogs (described herein).

Anti-osteometrin Antibodies

Human osteometrin proteins and polypeptides (or immunogenic fragments or analogs) can be used to raise antibodies useful in the invention; such polypeptides can be produced by recombinant or peptide synthetic techniques (see, e.g., *Solid Phase Peptide Synthesis*, supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a osteometrin protein or polypeptide. Host animals include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Antibodies within the invention include monoclonal antibodies, polyclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the osteometrin proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra).

In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., Monoclonal Antibodies and Cancer Therapy, Alan R. Liss, Inc., pp. 77–96, 1983). Such antibodies can be of any immunoglobulin class including IgG, IgM, IgE, IgA, IgD and any subclass thereof. The hybridoma producing the Mab of this invention may be cultivated in vitro or in vivo. The ability to produce high titers of mAbs in vivo makes this the presently preferred method of production.

Once produced, polyclonal or monoclonal antibodies are tested for specific osteometrin recognition by Western blot or immunoprecipitation analysis by standard methods, e.g., as described in Ausubel et al., supra. Antibodies that specifically recognize and bind to osteometrin are useful in the invention. For example, such antibodies can be used in an immunoassay to monitor the level of osteometrin produced by a mammal (for example, to determine the amount or subcellular location of osteometrin).

Preferably, antibodies of the invention are produced using fragments of the osteometrin protein which lie outside highly conserved regions and appear likely to be antigenic, by criteria such as high frequency of charged residues. In one specific example, such fragments are generated by standard techniques of PCR, and are then cloned into the PGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three separate fusion proteins can be generated, and each fusion can be injected into at least two rabbits. Antisera can be raised by injections in a series, preferably including at least three booster injections.

Antisera is also checked for its ability to immunoprecipitate recombinant osteometrin proteins or control proteins, such as glucocorticoid receptor, CAT, or luciferase.

The antibodies can be used, for example, in the detection of the osteometrin in a biological sample as part of a diagnostic assay, and also in evaluating the effectiveness of medical treatments by other therapeutic approaches. Antibodies also can be used in a screening assay to measure the effect of a candidate compound on expression or localization of osteometrin. Additionally, such antibodies can be used in conjunction with the gene therapy techniques described to, for example, evaluate the normal and/or engineered osteometrin-expressing cells prior to their being introduced into a patient. Such antibodies additionally can be used in a method for inhibiting abnormal osteometrin activity.

In addition, techniques developed for the production of "chimeric antibodies" (Morrison et al., Proc. Natl. Acad.

Sci., 81:6851, 1984; Neuberger et al., Nature, 312:604, 1984; Takeda et al., Nature, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine Mab and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against a osteometrin protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., Science, 246:1275, 1989) to allow rapid and easy identification of monoclonal Fab fragments with the desired specificity.

Antibodies to the osteometrin can, in turn, be used to generate anti-idiotype antibodies that resemble a portion of osteometrin using techniques well known to those skilled in the art (see, e.g., Greenspan et al., FASEB J. 7:437, 1993; Nissinoff, J. Immunol. 147:2429, 1991). For example, antibodies that bind to osteometrin and competitively inhibit the binding of a ligand of osteometrin can be used to generate anti-idiotypes that resemble a ligand binding domain of osteometrin and, therefore, bind and neutralize a ligand of osteometrin. Such neutralizing anti-idiotypic antibodies or Fab fragments of such anti-idiotypic antibodies can be used in therapeutic regimens.

Osteometrin Nucleic Acids as Therapeutic Agents

Nucleic acid sequences derived from osteometrin gene coding or regulatory sequences can be used as therapeutic agents. They can be DNA or RNA or chimeric mixtures or derivatives or modified versions thereof, single-stranded or double-stranded. They can in addition be derived from either the sense or anti-sense strand. The nucleic acid sequences can be modified at the base moiety, sugar moiety, or phosphate backbone, for example, to improve stability of the molecule, hybridization, etc. The nucleotides derived from osteometrin sequences may include other appended groups such as peptides (e.g., for targeting host cell receptors in vivo), or agents facilitating transport across the cell membrane (as described, e.g., in Letsinger et al., Proc. Natl. Acad. Sci. USA 86:6553, 1989; Lemaitre et al., Proc. Natl. Acad. Sci. USA 84:648, 1987; PCT Publication No. WO 88/09810) or the blood-brain barrier (see, e.g., PCT Publication No. WO 89/10134), or hybridization-triggered cleavage agents (see, e.g., Krol et al., BioTechniques 6:958, 1988), or intercalating agents (see, e.g., Zon, Pharm. Res. 5:539, 1988). To this end, an oligonucleotide can be conjugated to another molecule, e.g., a peptide, hybridization triggered cross-linking agent, transport agent, or hybridization-triggered cleavage agent.

The nucleotides containing osteometrin sequences may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The osteometrin nucleic acid sequences may also comprise at least one modified sugar moiety selected from the group including, but not limited to, arabinose, 2-fluoroarabinose, xylulose, and hexose.

In yet another embodiment, the osteometrin nucleic acid sequence comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the osteometrin nucleic acid sequence is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res. 15:6625, 1987). The oligonucleotide is a 2'-0-methylribonucleotide (Inoue et al., Nucl. Acids Res. 15:6131, 1987), or a chimeric RNA-DNA analog (Inoue et al., FEBS Lett. 215:327, 1987).

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448, 1988).

The nucleic acid molecules should be delivered to cells that express osteometrin in vivo, e.g., bone and dentin cells. A number of methods have been developed for delivering DNA or RNA to cells; e.g., molecules can be injected directly into the tissue site, or modified molecules, designed to target the desired cells (e.g., linked to peptides or antibodies that specifically bind receptors or antigens expressed on the target cell surface) can be administered systemically.

If intracellular concentrations of the molecule sufficient to suppress translation of endogenous mRNAs are not immediately achieved, a preferred approach uses a recombinant DNA construct in which the osteometrin nucleic acid sequence is placed under the control of a strong pol III or pol II promoter. The use of such a construct to transfect target cells in the patient will result in the transcription of sufficient amounts of single stranded RNAs that will form complementary base pairs with the endogenous osteometrin transcripts and thereby prevent translation of the osteometrin MRNA. For example, a vector can be introduced in vivo such that it is taken up by a cell and directs the transcription of an RNA. Such a vector can remain episomal or become chromosomally integrated, as long as it can be transcribed to produce the desired RNA.

Such vectors can be constructed by recombinant DNA technology methods standard in the art. Vectors can be plasmid, viral, or others known in the art, used for replication and expression in mammalian cells. Expression of the sequence encoding the RNA can be by any promoter known in the art to act in mammalian, preferably human cells. Such promoters can be inducible or constitutive. Such promoters include, but are not limited to: the SV40 early promoter region (Bernoist et al., Nature 290:304, 1981); the promoter contained in the 3' long terminal repeat of Rous sarcoma virus (Yamamoto et al., Cell 22:787–797, 1988); the herpes thymidine kinase promoter (Wagner et al., Proc. Natl. Acad. Sci. USA 78:1441, 1981); or the regulatory sequences of the metallothion gene (Brinster et al., Nature 296:39, 1988).

Any type of plasmid, cosmid, YAC, or viral vector can be used to prepare the recombinant DNA construct which can be introduced directly into the tissue site; e.g., the brain, heart, kidney, lung, uterus, endothelial cells, fibroblasts, and bone marrow stromal cells. Alternatively, viral vectors can be used that selectively infect the desired tissue (e.g., for brain, herpesvirus vectors may be used), in which case administration can be accomplished by another route (e.g., systemically).

Alternatively, endogenous osteometrin gene expression can be reduced by targeting deoxyribonucleotide sequences complementary to the regulatory region of the osteometrin gene (i.e., the osteometrin promoter and/or enhancers) to form triple helical structures that prevent transcription of the osteometrin gene in target cells in the body (Helene Anticancer Drug Des. 6:569, 1981; Helene et al., Ann. N.Y. Acad. Sci. 660:27, 1992; and Maher, Bioassays 14:807, 1992).

Identifying Proteins which Interact with Osteometrin

The invention also features proteins which interact with osteometrin. Any method suitable for detecting protein-protein interactions may be employed for identifying transmembrane proteins, intracellular, or extracellular proteins that interact with osteometrin. Among the traditional methods which may be employed are co-immunoprecipitation, crosslinking and co-purification through gradients or chromatographic columns of cell lysates or proteins obtained from cell lysates and the use of osteometrin to identify proteins in the lysate that interact with the osteometrin. For these assays, the osteometrin polypeptide can be a full length osteometrin, a soluble extracellular domain of osteometrin, or some other suitable osteometrin polypeptide. Once isolated, such an interacting protein can be identified and cloned and then used, in conjunction with standard techniques, to identify proteins with which it interacts. For example, at least a portion of the amino acid sequence of a protein which interacts with the osteometrin can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and PCR Protocols: A Guide to Methods and Applications, 1990, Innis et al., eds. Academic Press, Inc., New York).

Additionally, methods may be employed which result directly in the identification of genes which encode proteins which interact with osteometrin. These methods include, for example, screening expression libraries, in a manner similar to the well known technique of antibody probing of λgt11 libraries, using labeled osteometrin polypeptide or a osteometrin fusion protein, e.g., an osteometrin polypeptide or domain fused to a marker such as an enzyme, fluorescent dye, a luminescent protein, or to an immunoglobulin Fc domain.

There are also methods which are capable of detecting protein interaction. A method which detects protein interactions in vivo is the two-hybrid system (Chien et al., Proc. Natl. Acad. Sci. USA, 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding osteometrin, a osteometrin polypeptide, or a osteometrin fusion protein, and the other plasmid includes a nucleotide sequence encoding the transcription activator protein's activation domain fused to a CDNA encoding an unknown protein which has been recombined into this plasmid as part of a CDNA library. The DNA-binding domain fusion plasmid and the CDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, osteometrin may be used as the bait gene product. Total genomic or CDNA sequences are fused to the DNA encoding an activation domain. This library and a plasmid encoding a hybrid of bait osteometrin gene product fused to the DNA-binding domain are cotransformed into a yeast reporter strain, and the resulting transformants are screened for those that express the reporter gene. For example, a bait osteometrin gene sequence, such as osteometrin or a domain of osteometrin can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A CDNA library of the cell line from which proteins that interact with bait osteometrin gene product are to be detected can be made using methods routinely practiced in the art. According to the particular system described herein, for example, the CDNA fragments can be inserted into a vector such that they are translationally fused to the transcriptional activation domain of GAL4. This library can be co-transformed along with the bait osteometrin gene-GAL4 fusion plasmid into a yeast strain which contains a lacZ gene driven by a promoter which contains GAL4 activation sequence. A CDNA encoded protein, fused to GAL4 transcriptional activation domain, that interacts with bait osteometrin gene product will reconstitute an active GAL4 protein and thereby drive expression of the HIS3 gene.

Colonies which express HIS3 can then be purified from these strains, and used to produce and isolate the bait osteometrin gene-interacting protein using techniques routinely practiced in the art.

Applications for Osteometrin Polypeptides, Antibodies, Nucleic Acid Sequences, and Interacting Proteins Osteometrin proteins and polypeptides and osteometrin fusion proteins can be prepared for a wide range of uses including, but not limited to, generation of antibodies, preparation of reagents for diagnostic assays, identification of other molecules involved in inflammation, preparation of reagents for use in screening assays for inflammatory modulators, and preparation of therapeutic agents for treatment of bone-related disorders. For example, antibodies to osteometrin could be used as a way to monitor mineralization in individuals suffering from osteoporosis. In a second example, antibodies to osteometrin could be used in evaluating the effectiveness of medical treatments for bone and dental diseases. Molecules of the invention could also be used in other bone-related disorders such as osteopetrosis, osteogenesis imperfect, Paget's disease, and hyperparathyroidism.

RESULTS

I. Identification of Osteometrin

A. Extraction of Bone and Other Tissues

FIG. 1 depicts the protocol for extraction of bone. Each extraction was performed for 24 h at 4° C. in the presence of inhibitors (1 Mm phenylmethylsulfonyl fluoride, 1 Mm e-amino-n-caproic acid, 1 Mm p-hydorxymercuribenzoic acid, 1 mM benzamidine hydrochloride, mM levamisole, 5 mM sodium pyrophosphate). The cortical parts of calf tibiae (1–3 weeks postnatal) were crushed into powders, demineralized with HCl, constant pH 2.0, as described previously (Uchiyama et al., Biochem. 25:7572, 1986).

After centrifugation at 7,000 rpm (8,000×g), the residual demineralized bone powders were extracted with 0.5 M EDTA, 1.0 M NaCl in 50 mM Tris-HCl buffer. Additional Tris base added to maintain pH at 7.5. The residual bone powders was recovered and extracted with 1.0 M NaCl, 50 mM Tris-HCL, pH 7.4.

The NaCl-residue was extracted with 2 M guanidine HCL, 50 mM Tris-HCl, pH 7.4 for one day at 4° C. The 2 M guanidine HCl (2 M Gdn-HCl) extract was obtained by centrifugation followed by filtering through a glass microfiber membrane (Whatman) and then dialyzed against distilled water. The $H_2O$-soluble (2 M Gdn-HCl-ext-sup) and -insoluble (2 M Gdn-HCl-ext-ppt) fractions were separated by centrifugation and lyophilized. Similarly, the other extracts were also dialyzed and lyophilized. All the extracts were stored at −20° C. prior to use.

Calf dentin (1–2 weeks postnatal) was obtained after removal of enamel and cementum using diamond disk under liquid nitrogen. It was powdered, demineralized, and extracted with 0.5 EDTA/1.0 M NaCl and 2 M Gdn-HCl as described above. Rat bone powders were directly extracted with 4 M Gdn-HCl after HCl demineralization, while turkey tendons, bone tissues of chicken and fish were extracted following the complete protocol described for calf bone.

Calf articular cartilage and rat skin, muscle, liver, kidney, and brain were washed 0.15 M NaCl, 50 mM Tris-HCL, pH 7.4 and lyophilized. These soft tissues were extracted with 8 M urea, 2% SDS, 5% mercaptoethanol, 50 mM Tris-HCL, pH 6.8 at 100° C. for 5 min. Human blood from a healthy adult (male, 33 years old) and bovine serum were treated under the same conditions.

This aforementioned extraction approach allowed for selective extraction of the noncollagenous ECM bone proteins, thus contributing to the finding of the 35 kDa protein, a relatively minor component. For example, two major components, bone sialoprotein and osteopontin, were mainly extracted in the HCl-extract. Another major component, osteonectin, was predominantly solubilized in the EDTA/NaCl and NaCl extracts. On the other hand, osteocalcin, was observed in extracts of both the HCl-demineralizing and the NaCl extracts. In contrast, when the 2M Gdn-HCl-extract was dialyzed against $H_2O$ and centrifuged, the 35 kDa protein was observed as a major component.

The DE-52 column was able to remove proteoglycans, osteonectin, 36 kDa protein, and other minor components with molecular weights of 14–66 kDa. The 35 kDA protein was coeluted with type I collagen, and proteins of 25 kDa, 31 kDa, and 65 kDa in size. We observed that most of the collagen did not bind to the DE-52 column.

The TSK-3000 chromatography column separated the 35 kDa protein from the collagen and the 65 kDa protein.

B. Chromatographic Purification

The 2 M Gdn-HCl-ext-ppt was dissolved in 7 M urea, 50 mM Tris-HCl, pH 7.4, centrifuged, filtered through 0.45 μm membrane, and applied to a DE-52 column (2.5×5.5 cm) in the same buffer using a linear gradient of NaCl (0.0–0.5 M) at 4° C. The fractions containing the protein of interest were pooled and concentrated by ultrafiltration over a YM10 (Mr 10,000 cutoff, Amicon), and the buffer was changed to 7 M urea, 0.4 M NaCl, 50 mM $KH_2PO_4$, pH 6.8.

The sample was then chromatographed on a TSK-gel G3000SW (TSK-3000) HPLC column (0.75×60 cm, TosoHaas) in the same buffer at room temperature. The major fraction was passed through a Radial-Pak C4 reversed-phase (RP) HPLC column (8×100 mm, Waters) in 0.3% trifloroacetic acid using a linear gradient of 0–60% acetonitrile. The purified protein was dried using a Speed-vac drier.

The DE-52 column was able to remove proteoglycans, osteonectin, 36 kDa protein, and other minor components with molecular weights of 14–66 kDa. The 35 kDa protein was coeluted with type I collagen, and proteins of 25 kDa, 31 kDa, and 65 kDa in size. We observed that most of the collagen did not bind to the DE-52 column.

The TSK-3000 chromatography column separated the 35 kDa protein from the collagen and the 65 kDa protein. Upon SDS-PAGE (described infra), we found that about 90% of the protein was the 35 kDa protein, and the remaining 10% was made up by the 25 kDa, 31 kDa, and 65 kDa protein, collectively.

C. SDS-Polyacrylamide Gel Electrophoresis

SDS-polyacrylamide gel electrophoresis (PAGE)-SDS-PAGE was carried out by the method of Laemmli (Laemmli, Nature 227:680 1970), using 12.5% mini-gels (1.5×55×80 mm) at 9 mA for −4 h. All the samples were treated with β-mercaptoethanol unless indicated otherwise. The gels were stained with Coomassie brilliant blue R-250 (CBB) (Sigma).

II. Amino Acid Composition and Partial Sequence of the 35 kDa Protein

The chromatographically purified protein was electrophoresed, incubated with 10 mM 3-cyclohexylamino-1-propanesulfonic acid, 10% methanol, pH 9.7 for 30 min and transferred to an Immobilon PVDF membrane (Millipore) with a semi-dry transfer cell (Bio-Rad) for 2 h at a constant current density of 1 $mA/cm^2$ of gel. One portion (one lane) of the membrane was stained with CBB and the rest was washed with deionized distilled water and air-dried.

By comparing the stained membrane, the protein bands were cut out for analyses. The protein-containing strips were placed in a pyrex tube (6×50 mm), which was sealed in another pyrex tube (13×100 mm) containing 6 N HCl. Hydrolysis was carried out for 2 h and 24 h for phospho-amino acid and total amino acid analyses respectively. The hydrolysates were extracted with 0.1 N HCl, 30% methanol and analyzed using a Waters HPLC system and Pico Tag column (0.39×15 inch) as described (Salih et al., J. Biol. Chem. 271:16897).

The 35 kDa protein is similar in composition to many other bone ECM proteins in that it contains high contents of Asx and Glx. However, unlike the other proteins, it has high contents of Pro, Gly, Ala, Val and Leu (Table 1), indicating that the protein is hydrophobic. Consistent with this suggestion, we found the protein was poorly soluble in $H_2O$ under physiological conditions.

TABLE 1

Composition[a] of the 35 kDa protein

| | |
|---|---|
| Asx[b] | 166 |
| Thr | 37 |
| Ser | 71 |
| Glx[c] | 96 |
| Pro | 118 |
| Gly | 88 |
| Ala | 76 |
| Cys | ND[d] |
| Val | 78 |
| Met | ND |
| Ile | 35 |
| Leu | 70 |
| Tyr[e] | 5 |
| Phe | 15 |
| His | 38 |
| Lys | 27 |
| Arg | 81 |
| P-Ser[e] | 5 |
| P-Thr[e] | 0 |

[a]Residues/1000
[b]Asp + Asn
[c]Glu + Gln
[d]Not determined
[e]Uncorrected

The 35 kDA protein contains a high content of Arg residues. In addition, it has 5 phosphoserine residues per 1000 amino acid residues, which suggests it is phosphorylated. The phosphoproteins have been postulated to play an important role in bone formation (Glimcher et al., 1992, supra).

Peptide sequence analysis of the N-terminus and internal tryptic peptides revealed the following sequence information:

N-terminal sequence: Ser Tyr Pro Tyr Asn Pro Gln $Xaa_1$ $Xaa_2$ Met Asn Ile Tyr $Xaa_3$ $Xaa_4$ Tyr $Xaa_5$ Trp Phe Tyr $Xaa_6$ (SEQ ID NO:1), where $Xaa_1$ is Tyr or Gln, $Xaa_2$ is Val or Tyr, $Xaa_3$ is Asp or Pro, $Xaa_4$ is Phe or Val, $Xaa_5$ is Asn or Gly, and $Xaa_6$ is Leu, Asn, or Lys;

Internal peptide 1: Asn $Xaa_1$ Asp $Xaa_2$ Met $Xaa_3$ Gly (SEQ ID NO:2), where $Xaa_1$ is Asp or Tyr, $Xaa_2$ is Tyr, Met, or Asp, and $Xaa_3$ is Asp or Gly;

Internal peptide 2: Asn $Xaa_1$ $Xaa_2$ Leu $Xaa_3$ $Xaa_4$ $Xaa_5$ $Xaa_6$ Val Asp Phe Pro $Xaa_7$ Tyr (SEQ ID NO:3), where $Xaa_1$ is Val, Pro, or Met, $Xaa_2$ is Gln or Tyr, $Xaa_3$ is Glu or Pro, $Xaa_4$ is Gln or Gly, $Xaa_5$ is Met or Val, $Xaa_6$ is Gln, Asp, or Pro, and Xaa7 is Tyr or Pro;

Internal peptide 3: Val $Xaa_1$ Met $Xaa_2$ (SEQ ID NO:4), where $Xaa_1$ is Met, Gly, or Ala and $Xaa_2$ is Gly, Leu, or Tyr;

Internal peptide 4: Ala $Xaa_1$ Phe Gly $Xaa_2$ $Xaa_3$ $Xaa_4$ $Xaa_5$ Pro Val Gln Pro Gly (SEQ ID NO:5), where $Xaa_1$ is Val, Glu, or Ser, $Xaa_2$ is Pro or Leu, $Xaa_3$ is Pro or Glu, $Xaa_4$ is Gly or Asp, and $Xaa_5$ is Val or Pro;

Internal peptide 5: Tyr Ala Gly Tyr Asn Ala Tyr Ala Glu Gly (SEQ ID NO:6); and

Internal peptide 6: Asn $Xaa_1$ $Xaa_2$ Pro Asn Met Pro $Xaa_3$ Gly Pro (SEQ ID NO:7), where $Xaa_1$ is His or Leu, $Xaa_2$ is Pro or Gly, and $Xaa_3$ is any natural amino acid.

Because of the technical limitations of the peptide sequencer, certain residues could not be resolved. We named this protein osteometrin. Osteometrin is not homologous to any proteins in the SWISS-PROT or Genebank databases.

III. Generation and Characterization of Antibodies for Osteometrin

A. Generation of Anti-osteometrin Antibodies

The chromatographically purified protein was subject to SDS-PAGE, and the band corresponding to the 35 kDa protein was excised. The excised gel was dried, rehydrated with 0.9% sodium chloride, cut to small pieces (~0.5 mm), and mixed with Freud's complete adjuvant essentially following the method of Amero et al. (Amero et al., 1988, in New Protein Techniques, Walker ed., Humana Press, Glifton, p.355–62). The homogenate was injected into a rabbit, and a booster injection was done after three weeks. Two weeks after the second injection, the rabbit was bled. Antiserum was collected and stocked at −20° C.

B. Procedures for Western Blotting

Proteins separated by SDS-PAGE were incubated with 48 mM Trizma base, 39 mM glycine, 20% methanol and 1.3 mM SDS for 30 min and transferred to nitrocellulose membranes (Schleicher & Schuell). The membranes were blocked with 3% gelatin (Sigma) in 10 mM Tris-HCl, 150 mM NaCl, pH 8.0 for 4 h at room temperature, and reacted overnight with 1000 fold-diluted antibody against the protein of interest in the same buffer except 1% instead of 3% gelatin. The membranes were washed with the buffer containing 0.1% Tween-20, reacted with 1000 fold-diluted goat rabbit-IgG antibodies conjugated with alkaline phosphatase (Sigma) for 4 h, and the bound antibodies were visualized with 0.015% 5-bromo-4-chloro-3-indolyl phosphate and 0.03% nitroblue tetrazolium (Sigma) as substrates in 0.1 M $NaHCO_3$, 1.0 mM $MgCl_2$, pH 9.8.

C. Protein, Calcium and Phosphorus Determination

Protein quantification was carried out using Bio-Rad protein assay kit. Calcium and phosphorus were determined using Perkin-Elmer 603 atomic absorption spectrophotometer.

D. Characterization of the Anti-osteometrin Antibody

The anti-osteometrin antibody recognized a 35 kDa band. In addition, the anti-osteometrin antibody recognized proteins having molecular weights of 25 kDa, 31 kDa, and 60 kDa. Proteins of the same apparent molecular weights had also appeared following the final chromatographic step in purifying osteometrin. Collectively, the proteins having molecular weights of 25 kDa, 31 kDa and 60 kDa appeared to make up approximately 10% of the purified protein following the final chromatographic step.

Because all they all reacted with antibody raised against the 35 kDa protein, the 25 kDa and 31 kDa proteins were considered to be the fragments of the 35 kDa protein, and the 60 kDa protein an aggregation product of the 35 kDa protein with itself or one of its degraded forms. The extent of the aggregation appeared to be higher after purification, suggesting that in the crude materials some other proteins competitively bind to the 35 kDa protein and thereby inhibit the formation of the aggregated form, i.e. the 60 kDa protein.

The quantities of the 35 kDa protein and the 25 kDa protein showing immunoreactivity were considerably different, and no other proteins showed immunoreactivity.

Further evidence of multiple forms of the 35 kDa protein was obtained from subjecting the second major fraction recovered from DE-52 chromatography to gel electrophoresis. This fraction also contained the 35 kDa protein. Evidence for a protein existing in multiple forms during purification steps is observed in many other proteins such as osteopontin, bone sialoprotein, and 80 kDa glycosylated phosphoprotein.

E. Development of an Osteometrin ELISA Assay

A competitive enzyme-linked immunosorbent assay (ELISA) was developed as follows:

Miniwell-96 plates (Corning) were coated with 10 ng/well of osteometrin (OMN) in coating buffer (0.05 M $NaCO_3$, 0.05 M $NaHCO_3$, 0.05% $NaN_3$ [w/v]) at pH of 9.6. After overnight refrigeration, the protein solution was removed from the wells and the plate was blocked with 3% bovine serum albumin (BSA) in phosphate buffered saline ([PBS] 0.137 M NaCl, 2.7 mM KCl, 4 mM $Na_2HPO_4$, 1.5 mM $KH_2PO_4$, 0.05% $NaN_3$ [w/v]) at pH of 7.2 for 1.5 hours. The BSA solution was removed and the wells were washed 4 times for 3 minutes with PBS-T (PBS with 0.05% Tween-20), 50 µl of each standard ranging from 0 to 1000 ng/ml OMN was added to assigned wells in duplicate. Samples with end volume of 50 µl was added to other assigned wells. 50 µl of PBS-T was added to all the wells to make the volume up to 100 µl. 50 µl of a 1:5000 dilution of the primary mouse OMN antibody was added to each well and the plate was incubated overnight at 4° C. Plates were then washed 4 times with PBS-T. 100 µl of a 1:1000 diluted alkaline phosphatase conjugated rabbit anti-mouse antibody (Sigma) in PBS-T was added to each well and the plates were incubated for 1.5 hours. The plate was washed 4 times. 100 µl of substrate (0.5 mg/ml p-nitrophenylphosphate in coating buffer, pH 9.6) was added to each well. The plates were incubated for 1 hour. 50 µl of 1 N NaOH was added to terminate reaction. Absorbance at 405 nm was measured.

IV. Osteometrin Expression Patterns

A. Osteometrin is Expressed Almost Exclusively in Bone and Dentin Tissue

Western-blotting experiments using the anti-osteometrin antibody showed that the osteometrin protein was expressed almost exclusively in bone and dentin. Some osteometrin detected was detected in blood, and trace amounts were detected in two other active tissues, muscle and liver. No immunoreaction was observed in cartilage, skin, brain, and kidney.

The osteometrin protein observed in muscle and liver is probably derived from blood, as blood appears to contain higher quantities of osteometrin than do liver and muscle.

Unlike bone sialoprotein, osteopontin, osteocalcin, and fibronectin, osteometrin is poorly soluble in solution under physiological conditions.

Osteometrin's exclusive expression in bone and dentin tissue makes it, after osteocalcin and bone sialoprotein, only the third calcified tissue-specific protein. These proteins are expressed only in bone, dentin, cementum and other ectopic calcified tissues (Young et al., 1993, supra; Hauschka et al., 1989, Physiol. Rev. 69, 990–1047). Osteometrin's presence in blood, one of the most active tissues coupling bone formation and resorption, suggests it may be an indicator of bone metabolism.

B. Osteometrin is Expressed in Tissue Undergoing Calcification

To examine the relationship between osteometrin expression and calcification, osteometrin expression was examined in tissues undergoing calcification. Similar to bone, calcification and subsequent ossification occur in turkey tendon in vivo. However, the ossification process proceeds relatively slowly, thereby making it possible to obtain samples of turkey tendon at various stages of calcification before ossification begins. (Likins et al., 1960, in *Calcification in Biological Systems*, Sognaes, ed., Am. Assoc. Adv. Science, Washington, D.C., p. 143–149; Glimcher et al., Calcif. Tissue Int. 27:281, 1979).

Osteometrin was detected in tendon from 11 week-old turkeys. During this time calcium was also detectable. In 12 week-old turkeys, the calcium content increased, and the von Kosa staining was positive. At this stage, osteometrin was clearly observed. Thereafter, osteometrin levels increased.

The osteometrin pattern is quite similar to bone sialoprotein mRNA expression in cultured osteoblasts (Ibaraki et al., J. Bone Miner. Res. 7:743–54, 1992). Bone sialoprotein has been shown to act as a nucleator of calcium phosphate crystals in an agarose gel system (Hunter et al., Proc. Natl. Acad. Sci. USA 90:8562, 1994) and to stimulate the cell proliferation and differentiation and calcification in osteoblast-like MC3T3-E1 cells in vitro (Zhou et al., Calcif. Tissue Int. 56:403–07, 1995). These observations suggest that osteometrin may be involved in bone formation.

C. Osteometrin is Detectable in a Wide Range of Species

The antibody against osteometrin reacted with human blood, calcified turkey tendon, and bone tissues of rat, chicken and fish. The immunoreactive bands in turkey, chicken and fish were of a higher molecular weight, ~37 kDa, than the 35 kDa size observed in human, calf, and rat osteometrin.

The widespread species distribution of osteometrin contrasts with the narrower species distribution of antibodies reactive against osteonectin. Anti-bovine osteonectin antibody did not react with any of rat, chicken, or fish bone. Anti-chicken osteonectin did not react with bovine osteonectin. These data indicate that osteometrin occurs in a wide variety of species, probably in all the vertebrates, while the expression of osteonectin, one of the most highly conserved extracellular matrix proteins, is much more restricted.

Of an almost infinite variety of epitopes on protein molecules, only five complete structures have been analyzed by x-ray crystallography (Laver et al., Cell 61:553, 1990). Characteristically, these epitopes each contain between 15 and 22 residues on the antigen in contact with a similar number of residues on the antibody paratope. The antigenicity of the epitopes is dependent upon conformation of the native proteins.

In the present studies, the anti-osteometrin antibody was prepared using osteometrin that had been denatured with SDS. Nevertheless, the antibody was immunoreactive almost exclusively against calcified tissues in a wide variety of species.

These observations indicate the presence of highly conserved and specific domains in osteometrin. It is possible the anti-osteometrin antibody recognizes a functional domain analogous to Arg-Gly-Asp in bone sialoprotein and osteopontin. In these proteins the presence of the tri-peptide sequence is a prerequisite for the attachment of these proteins to cells. The motif is conserved between birds and mammals, and probably also in all the vertebrates (Young et al., 1993, supra; Gerstenfeld et al., Ann. N.Y. Acad. Sci. 760:67–82).

V. Osteometrin as a Marker for Bone Diseases

Figure 2:
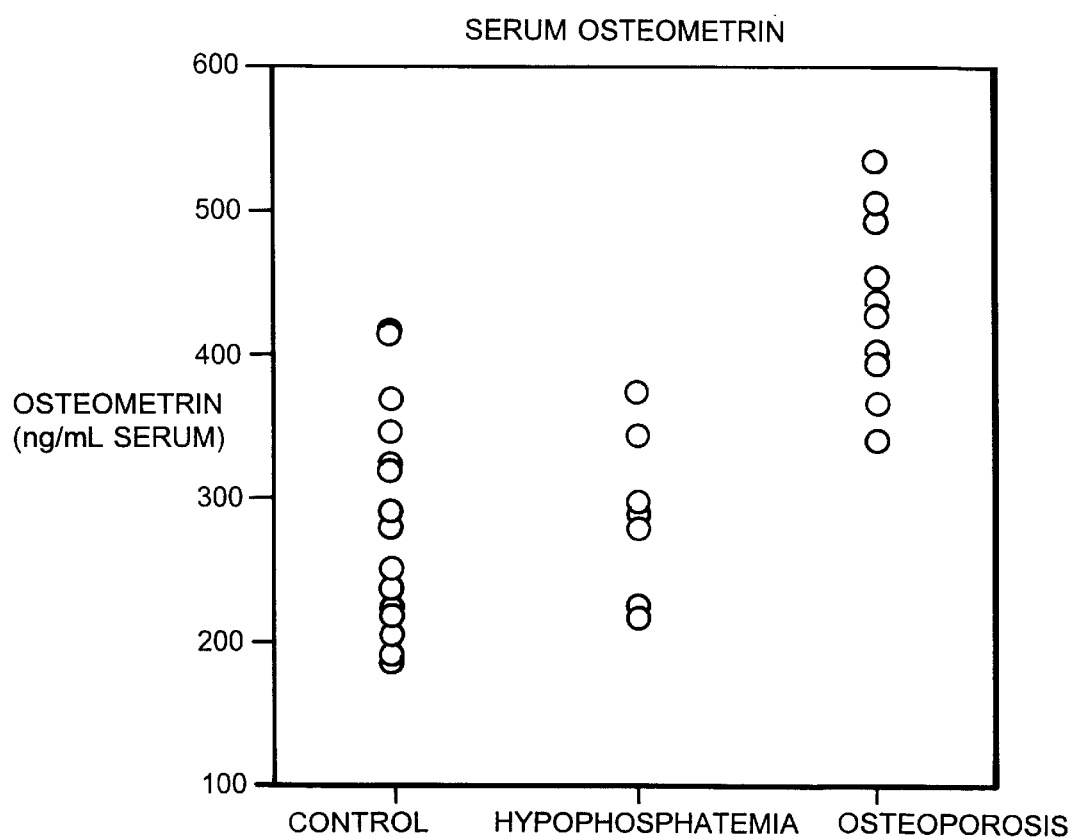
FIG. 2 describes serum osteometrin levels in osteoporotic patients.

To determine if osteometrin could be used as a marker for bone diseases, serum samples from osteoporosis patients, hypophosphatemia patients, and control individuals were subjected to osteometrin ELISA as described above. The amount of osteometrin found in these serum samples is graphed in FIG. 2. The level of osteometrin in osteoporotic patients are elevated in comparison with the control and hypophosphatemia patients. Thus, elevated serum osteometrin levels are correlated with osteoporosis.

In a separate experiment, the expression of osteometrin was measured in a human osteosarcoma cell line. The osteosarcoma cell line MG-63 was obtained from ATCC (NO. CRL-1427). MG-63 cells were grown for 2 weeks until reaching confluence in minimal essential medium with First strand cDNA was made from the RNA using SuperScript (Life Technologies, Grand Island, N.Y.). 1 μg of the total RNA with 1 μg of oligo dT was used per reaction. Reverse transcription was carried out as described in the manufacturer's instructions. Reverse transcriptase in the reaction was inactivated by heating to 95° C. for 5 min. Samples were diluted 50× and used for PCR.

PCR reactions were performed in a Progene Thermocycler (Cambridge, U.K.) with combinations of the degenerate primers (see Table 1) using TAQ DNA polymerase.

TABLE 1

| Primer (Amino Acid Sequence) | Primer Sequence |
| --- | --- |
| $N_1$-terminal-forward Ser Tyr Pro Tyr Asn Pro Gln Tyr Met Asn Ile (SEQ ID NO:8) | 5'-TAYCCNTAYAAYCCNYADCARTAYATGAA-3' (SEQ ID NO:9) |
| $N_2$-terminal-forward Ser Tyr Pro Tyr Asn Pro Tyr Val Tyr Met Asn Ile (SEQ ID NO:10) | 5'-TAYCCNTAYAAYCCNTAYGTNTAYATGAA-3' (SEQ ID NO:11) |
| Internal peptide 1-forward Asn Tyr Asp Met Gly (SEQ ID NO:12) | 5'-AAYTAYGAYGAYATGGGNGG-3' (SEQ ID NO:13) |
| Internal peptide 1-reverse | 5'-CCNCCCATRTCRTCRTARTT-3' (SEQ ID NO:14) |
| Internal peptide 2-forward Asn Met Tyr Leu Phe Gly Met Leu Val (SEQ ID NO:15) | 5'-AAYATGTAYYTDTTYGGNATGYTDGTN-3' (SEQ ID NO:16) |
| Internal peptide 2-reverse | 5'-NACHARCATNCCRAAHARRTACATRTT-3' (SEQ ID NO:17) |
| Internal peptide 4-forward Ala Ser Phe Gly Leu Glu Asp Pro Val Gln (SEQ ID NO:18) | 5'-TTYGGNYTDGARGAYCCNCCNGT-3' (SEQ ID NO:19) |
| Internal peptide 5-forward Tyr Ala Gly Tyr Met Ala Tyr Ala Glu Gly (SEQ ID NO:20) | 5'-GGNTAYATGGCNTAYGCNGARGG-3' (SEQ ID NO:21) |
| Internal peptide 5-reverse | 5'-CCYTCNGCRTANGCCATRTANCC-3' (SEQ ID NO:22) | essential amino acids (MEM), supplemented with 10% fetal bovine serum. Media was changed every 3 days. At confluence, media was switched to BGJb media supplemented with 10% fetal bovine serum. After 2 days this media was supplemented with 10 mM β-glycerohosphate, and after an additional 2 days this media was further supplemented with 12.5 μg/ml ascorbic acid. Cells were maintained in this media for 6 weeks.

Figure 4:
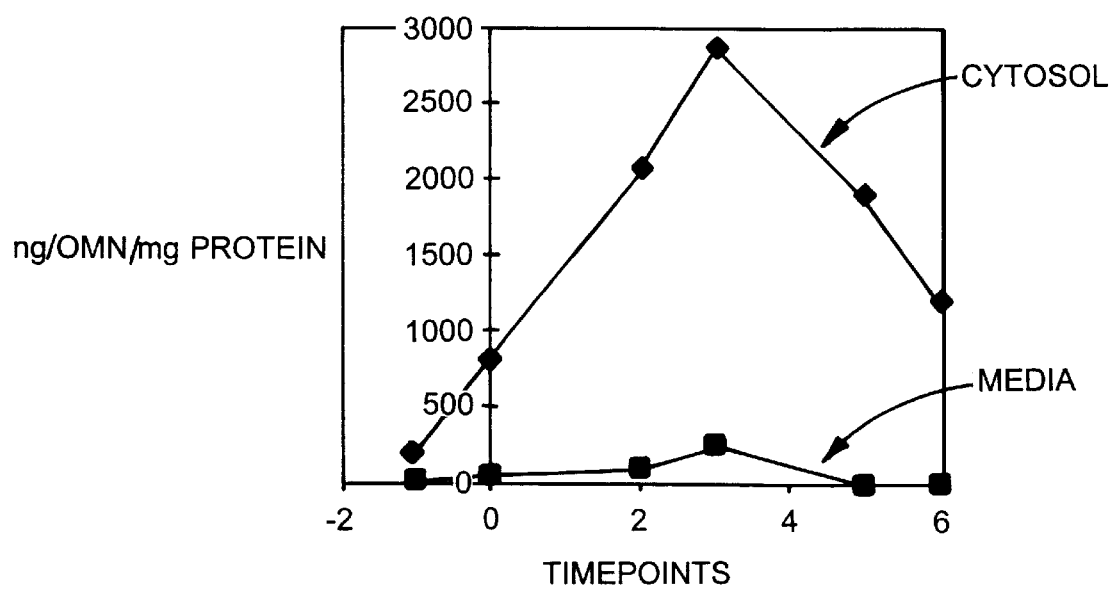
FIG. 4 is graph of osteometrin production in a osteosarcoma cell line.

FIG. 4 indicates the amount of osteometrin in cytosolic fractions or in the media during growth of the osteosarcoma cell line. Osteometrin was measured by ELISA. There is a rapid increase in osteometrin after changing to complete media, reaching a peak at the third week. After the third week there is a saturation of the protein in the cell matrix, and the production of osteometrin was decreased by the sixth week. Osteometrin is also found in the media, with an increase in the third week on complete media, then decreasing after the third week, following the same pattern as the cytosolic fraction. This result suggests that osteometrin is over-expressed by human bone cancer cells and that patients with bone cancer will exhibit elevated levels of osteometrin.

VI. Osteometrin cDNA

Total RNA from confluent bovine osteoblast primary cell cultures was isolated using Tri Reagent (Molecular Research Center, Inc., Cincinnati, Ohio.) according to manufacturer's instructions. Cell cultures were washed twice with ice cold PBS, and 1 ml of Tri Reagent was used for each 10 cm culture plate.

Degenerate primers were designed based on the amino acid sequences of the fragments from osteometrin. The least possible degeneracy was used to ensure specificity. Primers were 20–24 nucleotides in length and contained 50% GC so that PCR would be efficient.

Two-phase PCR was performed. PCR mixtures first underwent 5 cycles of low stringency amplification (typically 95° C., 1 min.; 37° C., 2 min.; and 72° C., 1 min.) to ensure sufficient priming by degenerate primers. In the second phase, samples were amplified for 35 cycles (95° C., 1 min.; 46° C., 1 min.; and 72° C., 1 min.). For the different sets of primers, the annealing temperatures in the first phase were varied at 2 degree increments to optimize specificity. PCR products were analyzed against 1 kb or 100 bp ladder markers in 1% agarose gels.

FIGS. 3A–3D are photographs of the PCR products after amplification. FIGS. 3A, 3B, and 3C represents the PCR products when the annealing temperature is 37° C., 39° C., and 42° C., respectively. Lanes for all three gels are as follows: 100 bp ladder (lane 1), $N_1$-terminal primer (lane 2), $N_2$-terminal primer (lane 3), internal peptide 1-reverse primer (lane 4), internal peptide 2-reverse primer (lane 5), $N_1$-terminal primer and internal peptide 1-reverse primer (lane 6), $N_2$-terminal primer and internal peptide 2-reverse primer (lane 7), $N_1$-terminal primer and internal peptide 2-reverse primer (lane 8), and $N_2$-terminal primer and internal peptide 2-reverse primer (lane 9). FIG. 3D is a photograph of PCR products (amplified using 37° C. as the annealing temperature) separated on a 1% agarose gel with the following lanes: 100 bp ladder (lane 1), internal peptide 5-reverse primer (lane 2), N$_1$-terminal primer and internal peptide 1-reverse primer (lane 3), internal peptide 1-forward primer (lane 4), N$_1$-terminal primer (lane 5), internal peptide 1-forward primer and internal peptide 5-reverse primer (lane 6).

A very strong band of 350 bp was produced with the internal peptide 1-forward primer and the internal peptide 5-reverse primer. This band was cloned into the pCR 2.1 plasmid and transformed into INVαF' cells (Invitrogen, Calif.). Other combinations of the degenerate primers described in Table 1 is used to amplify additional portions of the osteometrin cDNA.

The transformed cells can be plated and colonies analyzed for the presence of a osteometrin cDNA insert by standard molecular biology protocols. After isolating insert-positive cloned plasmids, the partial cDNA of osteometrin can be sequenced. In addition, the osteometrin cDNA clones can be used to produce labeled probes for northern blot analysis of various tissues from various vertebrates.

Other embodiments are within the following claims.

What is claimed is:

1. A substantially pure polypeptide comprising all of SEQ ID NOs:1–7, wherein SEQ ID NO:1 is positioned at the N-terminus of the polypeptide, each of SEQ ID NOs:2–7 is positioned C-terminal to SEQ ID NO:1, the polypeptide has a molecular weight of about 35–37 kilodaltons as indicated by polyacrylamide gel electrophoresis under denaturing conditions, and the polypeptide naturally occurs in a bone or dentin tissue of a vertebrate.

2. The polypeptide of claim 1, wherein the polypeptide is expressed in a bone tissue of a vertebrate.

3. The polypeptide of claim 1, wherein the polypeptide is expressed in dentin tissue.

* * * * *